United States Patent
Maalouf et al.

(10) Patent No.: US 11,449,802 B2
(45) Date of Patent: Sep. 20, 2022

(54) MACHINE-LEARNING BASED GESTURE RECOGNITION USING MULTIPLE SENSORS

(71) Applicant: Apple Inc., Cupertino, CA (US)

(72) Inventors: Charles Maalouf, Seattle, WA (US); Shawn R. Scully, Seattle, WA (US); Christopher B. Fleizach, Gilroy, CA (US); Tu K. Nguyen, San Jose, CA (US); Lilian H. Liang, Kenmore, WA (US); Warren J. Seto, Sunnyvale, CA (US); Julian Quintana, San Jose, CA (US); Michael J. Beyhs, San Francisco, CA (US); Hojjat Seyed Mousavi, Santa Clara, CA (US); Behrooz Shahsavari, Hayward, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/937,481

(22) Filed: Jul. 23, 2020

(65) Prior Publication Data
US 2021/0142214 A1 May 13, 2021

Related U.S. Application Data

(60) Provisional application No. 62/933,232, filed on Nov. 8, 2019.

(51) Int. Cl.
*G06V 10/00* (2022.01)
*G06N 20/00* (2019.01)
(Continued)

(52) U.S. Cl.
CPC ............. *G06N 20/00* (2019.01); *G06F 3/015* (2013.01); *G06F 3/017* (2013.01);
(Continued)

(58) Field of Classification Search
CPC ...... G06K 9/66; G06K 9/6254; G06K 9/6255; G06K 9/4628; G06K 9/32; G06K 9/2013;
(Continued)

(56) References Cited

U.S. PATENT DOCUMENTS 10,296,102 B1 * 5/2019 Misra ...................... G06T 7/215
10,600,334 B1 * 3/2020 Zhang ................. A63B 71/0622
(Continued)

OTHER PUBLICATIONS

Gupta et al., "Progression Modelling for Online and Early Gesture Detection," Cornell University Library, Sep. 2019.
(Continued)

*Primary Examiner* — Amir Alavi
(74) *Attorney, Agent, or Firm* — BakerHostetler

(57) ABSTRACT

A device implementing a system for machine-learning based gesture recognition includes at least one processor configured to, receive, from a first sensor of the device, first sensor output of a first type, and receive, from a second sensor of the device, second sensor output of a second type that differs from the first type. The at least one processor is further configured to provide the first sensor output and the second sensor output as inputs to a machine learning model, the machine learning model having been trained to output a predicted gesture based on sensor output of the first type and sensor output of the second type. The at least one processor is further configured to determine the predicted gesture based on an output from the machine learning model, and to perform, in response to determining the predicted gesture, a predetermined action on the device.

28 Claims, 9 Drawing Sheets

(51) Int. Cl.
*G06F 3/01* (2006.01)
*G06F 3/04883* (2022.01)
*G06K 9/62* (2022.01)
*G06N 3/08* (2006.01)

(52) U.S. Cl.
CPC ....... *G06F 3/04883* (2013.01); *G06K 9/6259* (2013.01); *G06N 3/08* (2013.01)

(58) Field of Classification Search
CPC .... G06K 9/344; G06K 9/6272; G06K 9/6259; G06K 9/00221; G06K 9/00335; G06F 3/015; G06F 3/017; G06F 3/0482; G06F 3/011; G06F 3/0304; G06F 3/0484; G06F 3/167; G06F 3/04883; G06N 99/005; G06N 20/00; G06N 3/08; H04N 7/0145; H04R 3/04
See application file for complete search history.

(56) References Cited

U.S. PATENT DOCUMENTS

| | | | |
|---|---|---|---|
| 10,620,713 B1* | 4/2020 | Ng | G06N 3/0454 |
| 10,725,733 B2* | 7/2020 | Nakagawa | G06F 3/017 |
| 10,809,796 B2* | 10/2020 | Armstrong-Muntner | G06F 3/017 |
| 11,036,303 B2* | 6/2021 | Rani | G06F 3/017 |
| 11,126,257 B2* | 9/2021 | Stent | G06F 3/017 |
| 11,126,283 B2* | 9/2021 | Chen | G06N 20/00 |
| 11,188,145 B2* | 11/2021 | Dong | G06F 3/017 |
| 2013/0257781 A1* | 10/2013 | Phulwani | G06F 3/042 345/173 |
| 2019/0196600 A1 | 6/2019 | Rothberg et al. | |
| 2019/0236465 A1 | 8/2019 | Vleugels | |
| 2019/0286233 A1 | 9/2019 | Newberry | |
| 2020/0142499 A1* | 5/2020 | Katz | G06F 3/013 |
| 2020/0337382 A1* | 10/2020 | Sur | G06K 9/6256 |
| 2021/0142214 A1* | 5/2021 | Maalouf | G06F 3/04883 |

OTHER PUBLICATIONS

International Search Report and Written Opinion from PCT/US2020/043333, dated Feb. 15, 2021, 22 pages.
Invitation to Pay Additional Fees from PCT/US2020/043333, dated Nov. 10, 2020, 15 pages.

* cited by examiner

MACHINE-LEARNING BASED GESTURE RECOGNITION USING MULTIPLE SENSORS

CROSS-REFERENCE TO RELATED APPLICATIONS

The present application claims the benefit of U.S. Provisional Patent Application Ser. No. 62/933,232, entitled "Machine-Learning Based Gesture Recognition Using Multiple Sensors," filed on Nov. 8, 2019, which is hereby incorporated by reference in its entirety for all purposes.

TECHNICAL FIELD

The present description relates generally to gesture recognition, including machine-learning based gesture recognition.

BACKGROUND

The present disclosure relates generally to electronic devices and in particular to detecting gestures made by a user wearing or otherwise operating an electronic device.

BRIEF DESCRIPTION OF THE DRAWINGS

Certain features of the subject technology are set forth in the appended claims. However, for purpose of explanation, several embodiments of the subject technology are set forth in the following figures.

DETAILED DESCRIPTION

The detailed description set forth below is intended as a description of various configurations of the subject technology and is not intended to represent the only configurations in which the subject technology can be practiced. The appended drawings are incorporated herein and constitute a part of the detailed description. The detailed description includes specific details for the purpose of providing a thorough understanding of the subject technology. However, the subject technology is not limited to the specific details set forth herein and can be practiced using one or more other implementations. In one or more implementations, structures and components are shown in block diagram form in order to avoid obscuring the concepts of the subject technology.

Electronic devices, such as smartwatches, may be configured to include various sensors. For example, a smartwatch may be equipped with one or more biosignal sensors (e.g., a photoplethysmogram (PPG) sensor), as well as other types of sensors (e.g., a motion sensor, an optical sensor, an audio sensor and the like). The various sensors may work independently and/or in conjunction with each other to perform one or more tasks, such as detecting device position, environmental conditions, user biological conditions and the like.

In some cases, a user may wish to use touch input (e.g., on a touchscreen of the electronic device) to perform an action. Alternatively or in addition, it may be desirable for a user to perform a gesture without having to rely on touch input. For example, a user may wish for the electronic device to perform a particular action based on a gesture performed by the same hand wearing the smartwatch.

The subject technology provides for detecting user gestures by utilizing outputs received via one or more sensors of the electronic device. For example, the electronic device may receive respective outputs from first sensor(s) (e.g., biosignal sensor(s)) and second sensor(s) (e.g., non-biosignal sensor(s)). The outputs may be provided as input to a machine learning model implemented on the electronic device, which had been trained based on outputs from various sensors, in order to predict a user gesture. Based on the predicted gesture, the electronic device may perform a particular action (e.g., changing a user interface). In one or more implementations, the machine learning model may be trained based on a general population of users, rather than a specific single user. In this manner, the model can be re-used across multiple different users even without a priori knowledge of any particular characteristics of the individual users. In one or more implementations, a model trained on a general population of users can later be tuned or personalized for a specific user.

Figure 1:
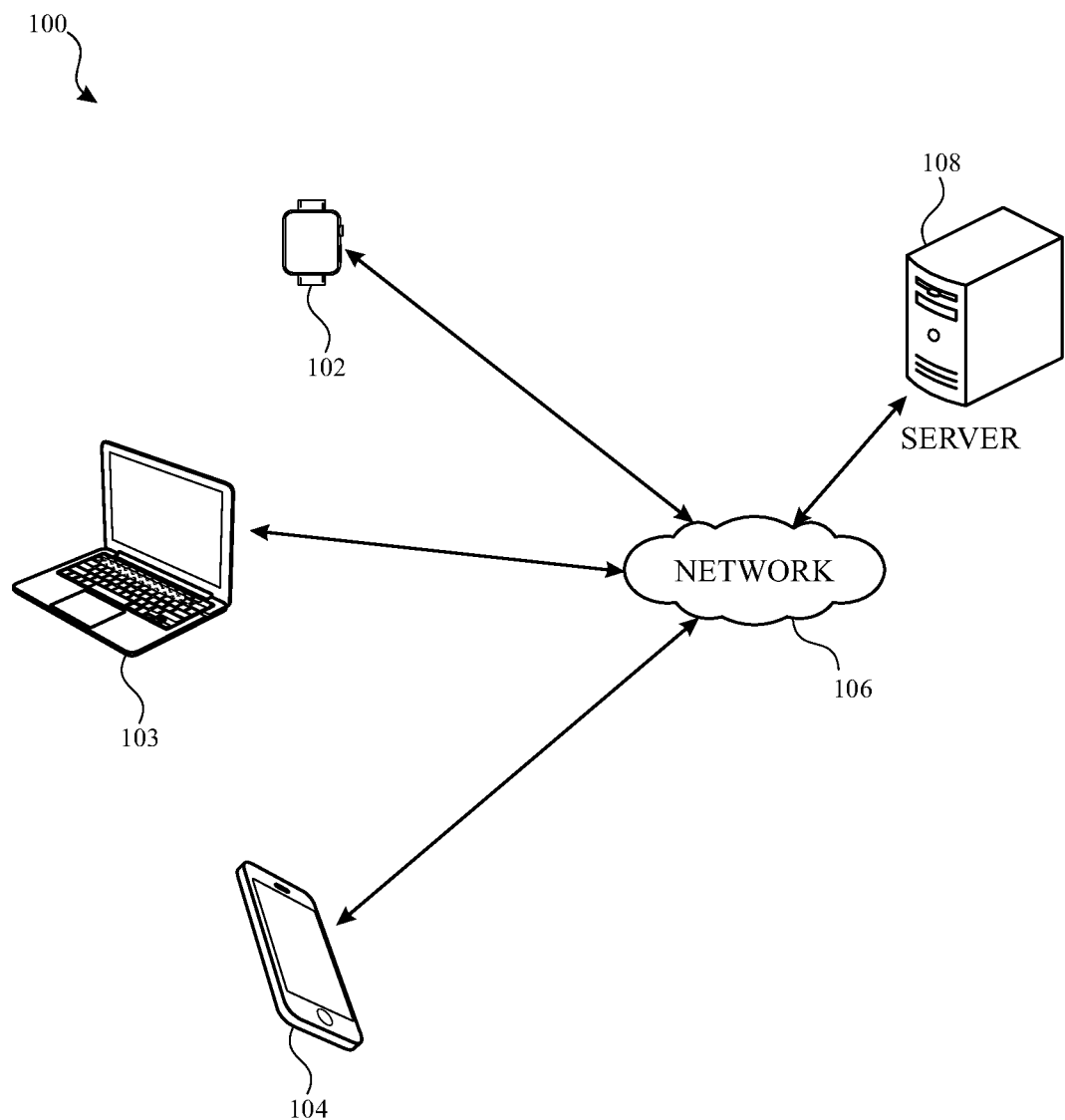
FIG. 1 illustrates an example network environment for providing machine-learning based gesture recognition in accordance with one or more implementations.

FIG. 1 illustrates an example network environment 100 for providing machine-learning based gesture recognition in accordance with one or more implementations. Not all of the depicted components may be used in all implementations, however, and one or more implementations may include additional or different components than those shown in the figure. Variations in the arrangement and type of the components may be made without departing from the spirit or scope of the claims as set forth herein. Additional components, different components, or fewer components may be provided.

The network environment 100 includes electronic devices 102, 103 and 104 (hereinafter 102-104), a network 106 and a server 108. The network 106 may communicatively (directly or indirectly) couple, for example, any two or more of the electronic devices 102-104 and the server 108. In one or more implementations, the network 106 may be an interconnected network of devices that may include, and/or may be communicatively coupled to, the Internet. For explanatory purposes, the network environment 100 is illustrated in FIG. 1 as including electronic devices 102-104 and a single server 108; however, the network environment 100 may include any number of electronic devices and any number of servers.

One or more of the electronic devices 102-104 may be, for example, a portable computing device such as a laptop computer, a smartphone, a smart speaker, a peripheral device (e.g., a digital camera, headphones), a tablet device, a wearable device such as a smartwatch, a band, and the like, or any other appropriate device that includes, for example, one or more wireless interfaces, such as WLAN radios, cellular radios, Bluetooth radios, Zigbee radios, near field communication (NFC) radios, and/or other wireless radios. In FIG. 1, by way of example, the electronic device 102 is depicted as a smartwatch, the electronic device 103 is depicted as a laptop computer, and the electronic device 104 is depicted as a smartphone.

As is discussed further below, each of the electronic devices 102-104 may include one or more sensors that can be used and/or repurposed to detect input received from a user. Each of the electronic devices 102-104 may be, and/or may include all or part of, the device discussed below with respect to FIG. 2, and/or the electronic system discussed below with respect to FIG. 10.

The server 108 may be, and/or may include all or part of the electronic system discussed below with respect to FIG. 10. The server 108 may include one or more servers, such as a cloud of servers. For explanatory purposes, a single server 108 is shown and discussed with respect to various operations. However, these and other operations discussed herein may be performed by one or more servers, and each different operation may be performed by the same or different servers. In one or more implementations, one or more of the electronic devices 102-104 may implement the subject system independent of the network 106 and/or independent of the server 108.

Figure 2:
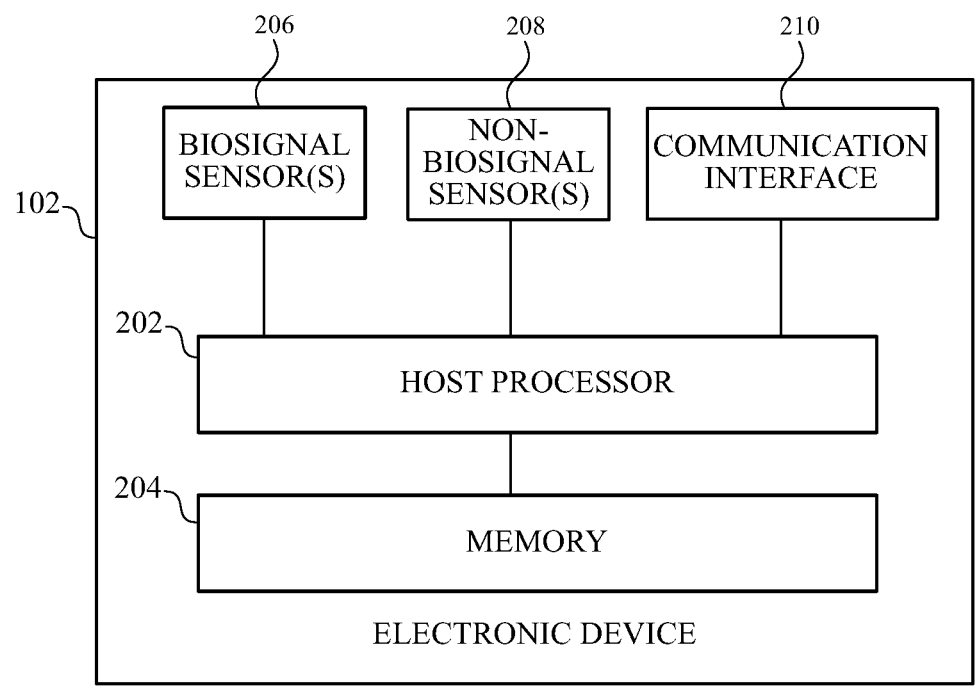
FIG. 2 illustrates an example device that may implement a system for machine-learning based gesture recognition in accordance with one or more implementations.

FIG. 2 illustrates an example device that may implement a system for machine-learning based gesture recognition in accordance with one or more implementations. For explanatory purposes, FIG. 2 is primarily described herein with reference to the electronic device 102 of FIG. 1. Not all of the depicted components may be used in all implementations, however, and one or more implementations may include additional or different components than those shown in the figure. Variations in the arrangement and type of the components may be made without departing from the spirit or scope of the claims as set forth herein. Additional components, different components, or fewer components may be provided.

The electronic device 102 may include a host processor 202, a memory 204, one or more biosignal sensor(s) 206, one or more non-biosignal sensor(s) 208, and a communication interface 210. The host processor 202 may include suitable logic, circuitry, and/or code that enable processing data and/or controlling operations of the electronic device 102. In this regard, the host processor 202 may be enabled to provide control signals to various other components of the electronic device 102. The host processor 202 may also control transfers of data between various portions of the electronic device 102. The host processor 202 may further implement an operating system or may otherwise execute code to manage operations of the electronic device 102.

The memory 204 may include suitable logic, circuitry, and/or code that enable storage of various types of information such as received data, generated data, code, and/or configuration information. The memory 204 may include, for example, random access memory (RAM), read-only memory (ROM), flash, and/or magnetic storage.

In one or more implementations, the biosignal sensor(s) 206 may include one or more sensors configured to measure biosignals. For example, the biosignal sensor(s) 206 may correspond to a photoplethysmography (PPG) PPG sensor configured to detect blood volume changes in microvascular bed of tissue of a user (e.g., where the user is wearing the electronic device 102 on his/her body, such as his/her wrist). The PPG sensor may include one or more light-emitting diodes (LEDs) which emit light and a photodiode/photodetector (PD) which detects reflected light (e.g., light reflected from the wrist tissue). The biosignal sensor(s) 206 are not limited to a PPG sensor, and may additionally or alternatively correspond to one or more of: an electroencephalogram (EEG) sensor, an electrocardiogram (ECG) sensor, an electromyogram (EMG) sensor, a mechanomyogram (MMG) sensor, an electrooculography (EOG) sensor, a galvanic skin response (GSR) sensor, a magnetoencephalogram (MEG) sensor and/or other suitable sensor(s) configured to measure biosignals.

In one or more implementations, the non-biosignal sensor(s) 208 may include one or more sensors for detecting device motion, sound, light, wind and/or other environmental conditions. For example, the non-biosignal sensor(s) 208 may include one or more of: an accelerometer for detecting device acceleration, an audio sensor (e.g., microphone) for detecting sound, an optical sensor for detecting light, and/or other suitable sensor(s) configured to output signals indicating device state and/or environmental conditions.

As discussed further below with respect to FIGS. 3-9, one or more of the electronic devices 102-104 may be configured to output a predicted gesture based on output provided by the biosignal sensor(s) 206 and/or output by the non-biosignal sensor(s) 208 (e.g., corresponding to inputs detected by the biosignal sensor(s) 206 and the non-biosignal sensor(s) 208).

The communication interface 210 may include suitable logic, circuitry, and/or code that enables wired or wireless communication, such as between the electronic device 102 and other device(s). The communication interface 210 may include, for example, one or more of a Bluetooth communication interface, an NFC interface, a Zigbee communication interface, a WLAN communication interface, a USB communication interface, or generally any communication interface.

In one or more implementations, one or more of the host processor 202, the memory 204, the biosignal sensor(s) 206, the non-biosignal sensor(s) 208, the communication interface 210, and/or one or more portions thereof, may be implemented in software (e.g., subroutines and code), may be implemented in hardware (e.g., an Application Specific Integrated Circuit (ASIC), a Field Programmable Gate Array (FPGA), a Programmable Logic Device (PLD), a controller, a state machine, gated logic, discrete hardware components, or any other suitable devices) and/or a combination of both.

Figure 3:
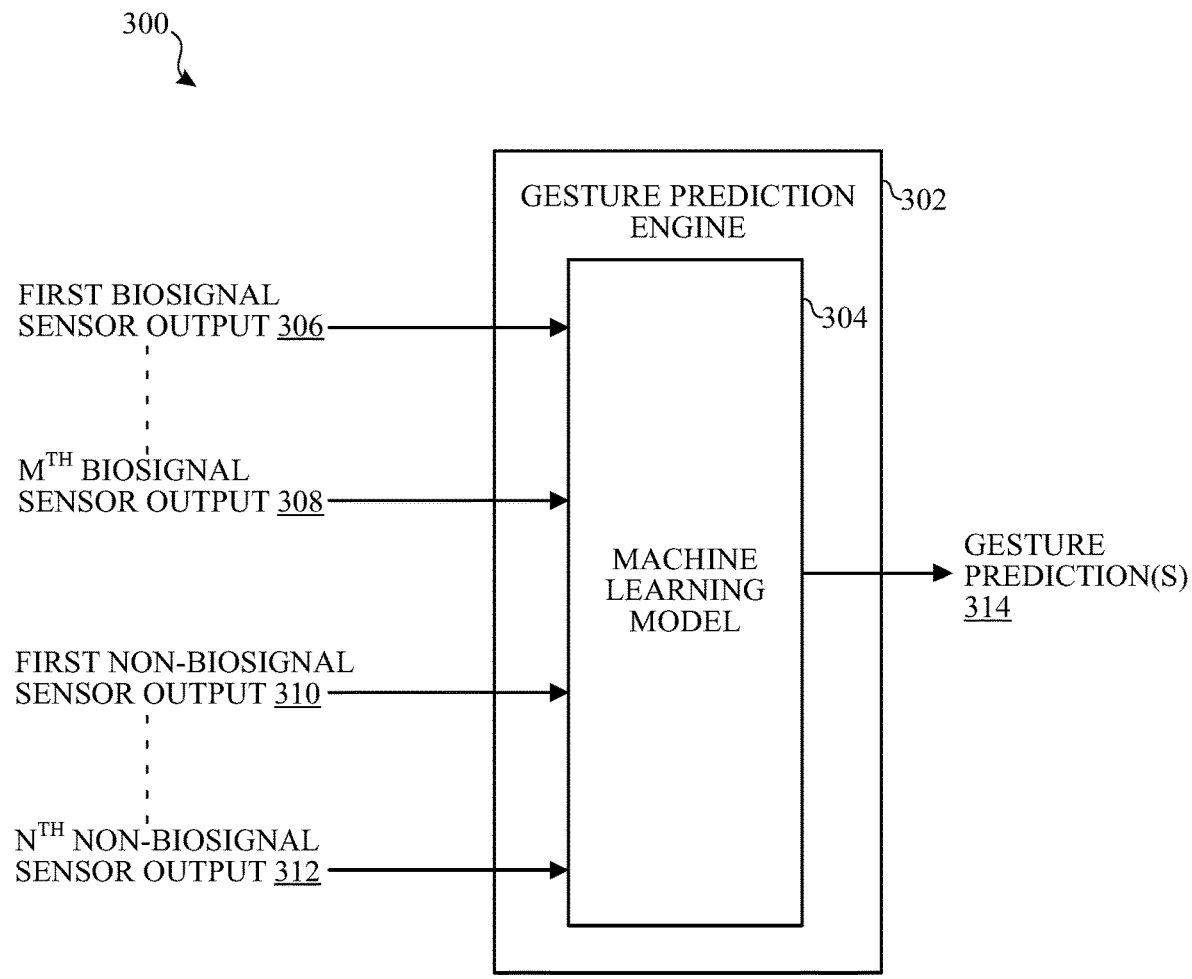
FIG. 3 illustrates an example architecture, that may be implemented by an electronic device, for machine-learning based gesture recognition in accordance with one or more implementations.

FIG. 3 illustrates an example architecture 300, that may be implemented by an electronic device, for machine-learning based gesture recognition in accordance with one or more implementations. Not all of the depicted components may be used in all implementations, however, and one or more implementations may include additional or different components than those shown in the figure. Variations in the arrangement and type of the components may be made without departing from the spirit or scope of the claims as set forth herein. Additional components, different components, or fewer components may be provided.

As illustrated, the gesture prediction engine 302 includes a machine learning model 304. The machine learning model 304, in an example, is implemented as a neural network (NN) model that is configured to detect a gesture using such sensor inputs over time. As discussed herein, a neural network (NN) is a computing model that uses a collection of connected nodes to process input data based on machine learning techniques. Neural networks are referred to as networks because they may be represented by connecting together different operations. A model of a NN (e.g., feed-forward neural network) may be represented as a graph representing how the operations are connected together from an input layer, through one or more hidden layers, and finally to an output layer, with each layer including one or more nodes, and where different layers perform different types of operations on respective input.

In one or more implementations, the machine learning model 304 is implemented as a convolutional neural network (CNN). As discussed herein, a CNN refers to a particular type of neural network, but uses different types of layers made up of nodes existing in three dimensions where the dimensions may change between layers. In a CNN, a node in a layer may only be connected to a subset of the nodes in a previous layer. The final output layer may be fully connected and be sized according to the number of classifiers. A CNN may include various combinations, and in some instances, multiples of each, and orders of the following types of layers: the input layer, convolutional layers, pooling layers, rectified linear unit layers (ReLU), and fully connected layers. Part of the operations performed by a convolutional neural network includes taking a set of filters (or kernels) that are iterated over input data based on one or more parameters.

In an example, convolutional layers read input data (e.g., a 3D input volume corresponding to sensor output data, a 2D representation of sensor output data, or a 1D representation of sensor output data), using a kernel that reads in small segments at a time and steps across the entire input field. Each read can result in an input that is projected onto a filter map and represents an internal interpretation of the input. A CNN such as the machine learning model 304, as discussed herein, can be applied to human activity recognition data (e.g., sensor data corresponding to motion or movement) where the CNN model learns to map a given window of signal data to an activity (e.g., gesture and/or portion of a gesture) where the model reads across each window of data and prepares an internal representation of the window.

The machine learning model 304 may be configured to receive output from one, two or more than two sensors (e.g., at least one biosignal sensor and/or at least one non-biosignal sensor) as input. As shown in the example of FIG. 3, the machine learning model 304 receives first biosignal sensor output 306 to $M^{th}$ biosignal sensor output 308, as well as first non-biosignal sensor output 310 to $N^{th}$ non-biosignal sensor output 312, as input.

The first biosignal sensor output 306 to the $M^{th}$ biosignal sensor output 308 includes output from one or more of the biosignal sensor(s) 206. As noted above, the biosignal sensor(s) 206 may correspond to a PPG sensor (e.g., for detecting blood volume changes) and/or other types of sensor(s) configured to output biosignals. Moreover, the first non-biosignal sensor output 310 to $N^{th}$ non-biosignal sensor output 312 includes output from one or more of the non-biosignal sensor(s) 208. As noted above, the non-biosignal sensor(s) 208 may correspond to one or more of an accelerometer, an optical sensor, an audio sensor (e.g., a microphone) and/or other types of sensor(s) configured to output signals indicating device state and/or environmental conditions.

In one or more implementations, one or more of the sensor outputs 306-312 may correspond to a window of time (e.g., 0.5 seconds, 0.1 seconds, or any window of time) in which sensor data was collected by the respective sensor. Moreover, the sensor outputs 306-312 may be filtered and/or pre-processed (e.g., normalized) before being provided as inputs to the machine learning model 304.

In one or more implementations, the sensor outputs 306-312 may be used to indicate a gesture performed by the user. For example, the gesture may correspond to a single-handed gesture performed by the same hand that is coupled to (e.g., wearing) the electronic device 102. The gesture may correspond to a static gesture (e.g., a specific type of hand/finger positioning that is held for a predefined time period) and/or a dynamic gesture (e.g., a motion-based gesture performed over a predefined time period). Moreover, the gesture may correspond to a finger-based gesture (e.g., in which the fingers move and/or are positioned in a specific manner), a wrist-based gesture (e.g., in which the wrist moves and/or is positioned in a specific manner) and/or a combination of a finger-based and wrist-based gesture. In one or more implementations, the gesture may correspond to a gesture performed on a horizontal and/or vertical surface, such as, for example, a table, a wall, a floor, and/or another hand.

Moreover, the sensor outputs 306-312 may individually and/or collectively be used by the machine learning model 304 to indicate a specific type of user gesture. As noted above, one or more of the biosignal sensor(s) 206 may correspond to a PPG sensor configured to detect blood volume changes. For example, variations in blood volume may indicate different user gestures (e.g., where particular blood volume changes map to respective types of user gestures). As further noted above, the machine learning model 304 may receive non-biological signal output (e.g., the non-biosignal sensor outputs 310-312), which may be used in conjunction with the biosignal sensor output(s) 306-308, as supplemental information predict the specific gesture. For example, the non-biosignal sensor outputs 310-312 may indicate false positives for gesture predictions otherwise indicated by the biosignal sensor outputs 306-308.

The machine learning model 304 (e.g., a CNN) may have been trained (e.g., pre-trained) on different device(s) (e.g., one or more smartwatches other than the electronic device 102) based on sensor output data prior to being deployed on the electronic device 102. The sensor output data for training may correspond to output from one or more biosignal sensor(s) (e.g., similar to the biosignal sensor(s) 206) and/or from one or more non-biosignal sensors (e.g., similar to the non-biosignal sensor(s) 208). In one or more implementations, the machine learning model 304 may have been trained across multiple users, for example, who provided different types of gestures while wearing a device (e.g., another smartwatch with biosignal and/or non-biosignal sensor(s)) and confirmed the gestures (e.g., via a training user interface) as part of a training process. In this manner, the machine learning model may be used, in one or more implementations, to predict gestures across a general population of users, rather than one specific user.

After the machine learning model 304 has been trained, the machine learning model 304 may generate a set of output predictions corresponding to gesture prediction(s) 314. After the predictions are generated, a policy may be applied to the predictions to determine whether to indicate an action for the electronic device 102 to perform, which is discussed in more detail with respect to FIGS. 4A-4B.

Figure 4A:
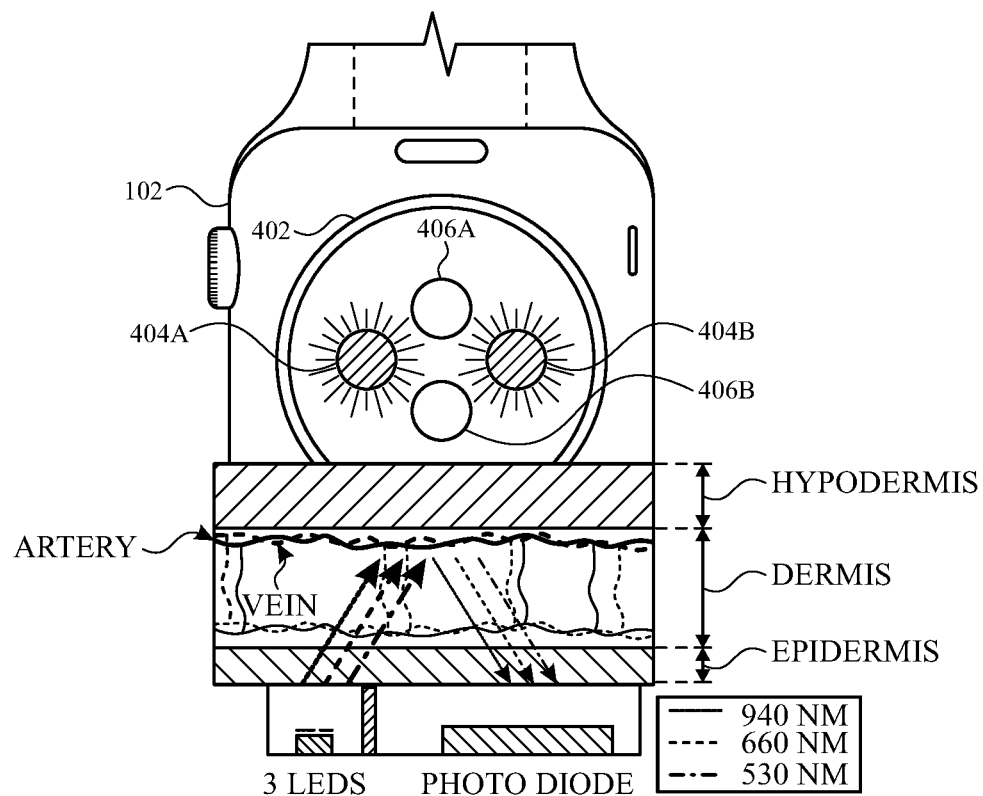
FIGS. 4A-4B illustrate example diagrams of respective sensor outputs of an electronic device that may indicate a gesture in accordance with one or more implementations.
Figure 4B:
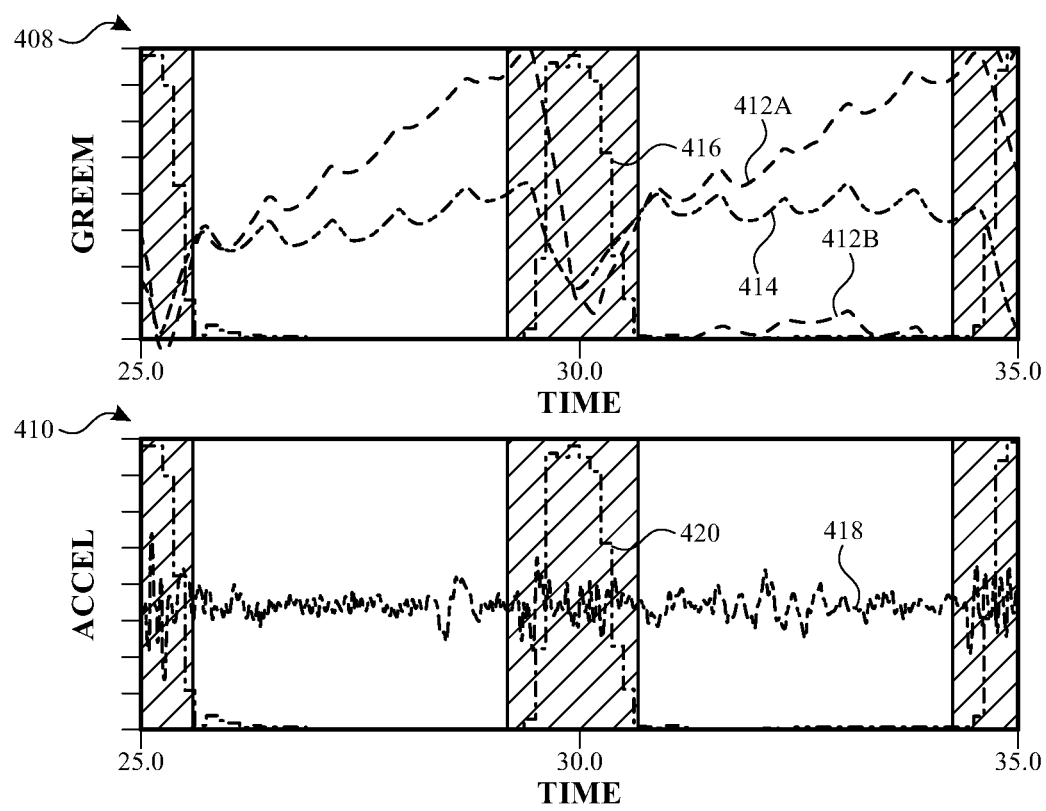

FIGS. 4A-4B illustrate example diagrams of respective sensor outputs of an electronic device that may indicate a gesture in accordance with one or more implementations. For explanatory purposes, FIGS. 4A-4B are primarily described herein with reference to the electronic device 102 of FIG. 1. However, FIGS. 4A-4B are not limited to the electronic device 102 of FIG. 1, and one or more other components and/or other suitable devices (e.g., any of the electronic device 102-104) may be used instead.

FIG. 4A illustrates an example in which the electronic device 102 includes a PPG sensor 402. The PPG sensor 402 includes one or more light sources 404A-404B (e.g., LEDs) configured to emit light. For example, the light source 404A may emit light corresponding to a first frequency (e.g., green light) and the light source 404B may emit light corresponding to a second frequency (e.g., another color such as brown and/or infrared light). The PPG sensor 402 further includes one or more photodiodes 406A-406B configured to detect reflected light (e.g., light reflected from wrist tissue of the user, based on light emitted by the light sources 404A-404B). The PPG sensor 402 may be configured to average or otherwise process the output from the photodiodes 406A-406B to provide output (e.g., the first biosignal sensor output 306) corresponding to blood volume changes. The electronic device 102 may further include an accelerometer (not shown) configured to detect device acceleration.

FIG. 4B illustrates example timing diagrams 408-410 of respective sensor outputs of the electronic device 102, together with respective confidence levels corresponding to a particular user gesture. For example, the timing diagrams 408-410 may indicate the confidence of a fist-clinch gesture.

The timing diagram 408 illustrates sensor output of the PPG sensor 402 of the electronic device 102 together with confidence output (e.g., based on the machine learning model 304) that the sensor output corresponds to a particular user gesture (e.g., fist-clinch). Sensor outputs 412A-412B correspond to reflected light detected by the photodiodes 406A-406B based on light emitted by the light sources 404A-404B. While FIG. 4B illustrates the example of a light source which is green, the PPG may include alternative and/or additional light sources (e.g., other colors such as brown, infrared light, and the like). The sensor output 414 corresponds to an average of the sensor outputs 412A-412B. Moreover, the confidence output 416 (e.g., based on the machine learning model 304) indicates that the sensor output corresponds to a particular user gesture.

In one or more implementations, the timing diagram 410 illustrates sensor output of an accelerometer of the electronic device 102 together with confidence output (e.g., by the machine learning model 304) that the sensor output corresponds to a particular user gesture (e.g., fist-clinch). The sensor output 418 corresponds to detected acceleration (e.g., based on device movement). Moreover, the confidence value 420 indicates the calculated confidence (e.g., based on the machine learning model 304) that the sensor output indicates a particular user gesture.

In one or more implementations, the machine learning model 304 may be configured to provide gesture prediction(s) (e.g., corresponding to gesture prediction(s) 314) on a periodic basis (e.g., 10 predictions per second, or some other amount of predictions per time period) based on the aforementioned sensor output data which is visually shown in the timing diagrams 408-410. While FIGS. 4A-4B are described with respect to the example of a fist-clinch gesture, the machine learning model 304 may be configured to provide gesture predictions with respect to multiple different types of gestures (e.g., static and/or dynamic finger-based gestures, static and/or dynamic wrist-based gestures).

In one or more implementations, as mentioned above, the machine learning model 304 may utilize a policy to determine a prediction output. As referred to herein, a policy can correspond to a function that determines a mapping of a particular input (e.g., sensor output data) to a corresponding action (e.g., providing a respective prediction). For example, the machine learning model 304 may utilize sensor output data corresponding to a particular gesture to make a classification, and the policy can determine an average of a number of previous predictions (e.g., 5 previous predictions). The machine learning model 304 may take the previous predictions over a window of time, and when the average of these predictions exceeds a particular threshold, the machine learning model 304 can indicate a particular action (e.g., updating a user interface) for the electronic device 102 to initiate. In one or more implementations, the policy may be applied to an output of the machine learning model 304.

In one or more implementations, a state machine may be utilized to further refine the predictions output by the machine learning model 304 (e.g. based on previous predictions over a window of time). For example, the state machine may include one or more transitional states between a gesture detected and a gesture not detected, such as start of gesture detected, middle of gesture detected, end of gesture detected, and the like.

Figure 5:
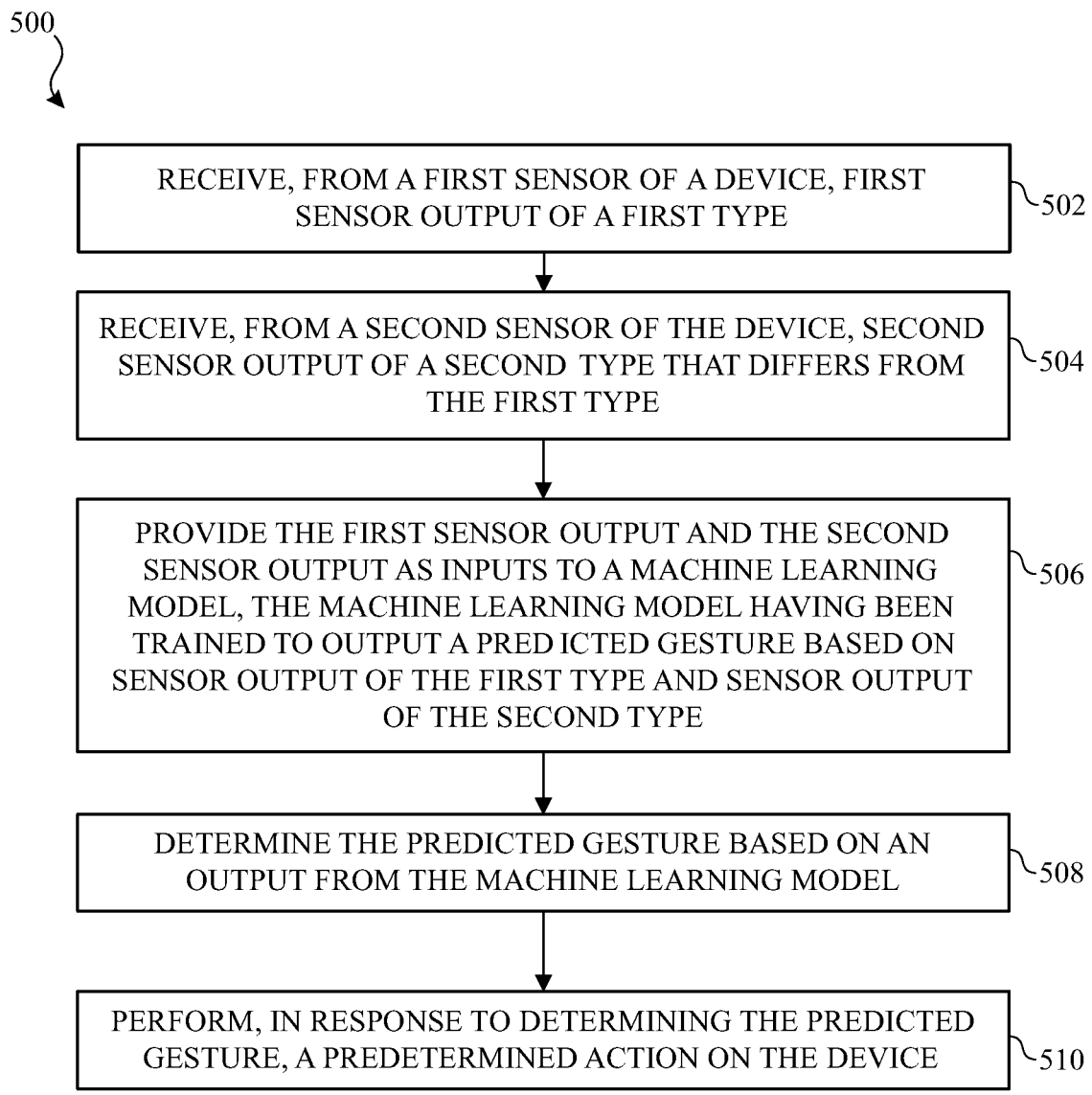
FIG. 5 illustrates a flow diagram of example process for machine-learning based gesture recognition in accordance with one or more implementations.

FIG. 5 illustrates a flow diagram of example process for machine-learning based gesture recognition in accordance with one or more implementations. For explanatory purposes, the process 500 is primarily described herein with reference to the electronic device 102 of FIG. 1. However, the process 500 is not limited to the electronic device 102 of FIG. 1, and one or more blocks (or operations) of the process 500 may be performed by one or more other components and other suitable devices (e.g., any of the electronic devices 102-104). Further for explanatory purposes, the blocks of the process 500 are described herein as occurring in serial, or linearly. However, multiple blocks of the process 500 may occur in parallel. In addition, the blocks of the process 500 need not be performed in the order shown and/or one or more blocks of the process 500 need not be performed and/or can be replaced by other operations.

The electronic device 102 receives, from one or more of the biosignal sensor(s) 206, first sensor output of a first type (502). The biosignal sensor(s) 206 of the device may be a photoplethysmography (PPG) sensor. The PPG sensor may include at least one of an infrared light source or a color light source. In one or more implementations, the first sensor output may indicate a change in blood flow.

The electronic device 102 receives, from one or more of the non-biosignal sensor(s) 208, second sensor output of a second type that differs from the first type (504). The non-biosignal sensor(s) 208 may be an accelerometer and/or a microphone. At least one of receiving the first sensor output or receiving the second sensor output may be based on a determination that the device is in a gesture detection mode.

The electronic device 102 provides the first sensor output and the second sensor output as inputs to a machine learning model, the machine learning model having been trained to output a predicted gesture based on sensor output of the first type and sensor output of the second type (506). The machine learning model may have been trained across multiple users.

The electronic device 102 determines the predicted gesture based on an output from the machine learning model (508). The predicted gesture may be at least one of a finger-based gesture, or a wrist-based gesture. For example, the finger-based gesture may be at least one of a finger pinch gesture (e.g., touching two fingers together), a double pinch or other multiple pinch (e.g., touching two fingers together multiple times with a separation of the two fingers in between the multiple touches), a fist-clinch gesture (e.g., holding one or more (or all) fingers and/or thumb in the form of a fist), and/or a double-clinch gesture or other multiple clinch gesture. For example, the wrist-based gesture may be at least one of a knock gesture or a double knock gesture.

The electronic device 102 performs, in response to determining the predicted gesture, a predetermined action on the device (510). The predetermined action may correspond to changing a user interface on the device. These predetermined actions can provide, in one or more implementations, gesture-powered switch control (e.g., for accessibility) for an electronic device. For example, gesture-powered switch control can allow a user to navigate an operating system of a smartwatch using only the watch-wearing arm. Gesture-powered switch control can include operating a user interface (UI) element that is highlighted by a selector, by performing a gesture while the UI element is highlighted by the selector.

The predetermined actions can also enable users to set shortcuts that are accessed uniquely by corresponding gestures. For example, shortcuts having associated gestures can be provided automatically by context (e.g., including shortcuts and corresponding gestures for interacting with a media player application, shortcuts and corresponding gestures for interacting with a workout application, and/or shortcuts and corresponding gestures for interacting with any other application).

The predetermined actions can also include providing instructions to a companion device (e.g., a mobile phone, a laptop, a tablet, another wearable device, etc. that is communicatively coupled to a wearable gesture-detecting device such as a smartwatch), to enable gesture-based control of the companion device. For example, a predetermined action responsive to a predicted gesture can include sending gesture information or an instruction to a companion device that is playing media (e.g., audio or video) to skip to a next or previous track or chapter, pause or restart the media, or perform other medial control operations at the companion device. As another example, a predetermined action responsive to a predicted gesture can include sending gesture information or an instruction to a companion device that is displaying a browser or a document to scroll or perform other control of the browser or document. As another example, a predetermined action responsive to a predicted gesture can include sending gesture information or an instruction to a companion device that is running an augmented reality application or a virtual reality application, for input to or control of the application.

In one or more implementations, a machine learning model for gesture prediction and/or identification can include a portion that initially predicts whether the model should be in a gesture detection mode. For example, the machine learning models described above in connection with FIGS. 1-5 can include a prediction head in the neural network that predicts whether the remaining portions of the model (or a separate model) should start model prediction or not. This additional prediction head can be helpful, for example, to save energy and computation time (e.g., to help allow gesture detection to constantly run in the background even on devices with limited power supplies such as batteries). In this way, machine learning models can be provided for which the data cube does not have to perform operations all the way down to the end of the network if the additional gesture-detection head indicates that a gesture is not occurring. The prediction head for determining whether the model proceeds to a gesture prediction mode can be trained in a common training operation with other portions of the model, or trained separately from a separate gesture prediction model.

Figure 6:
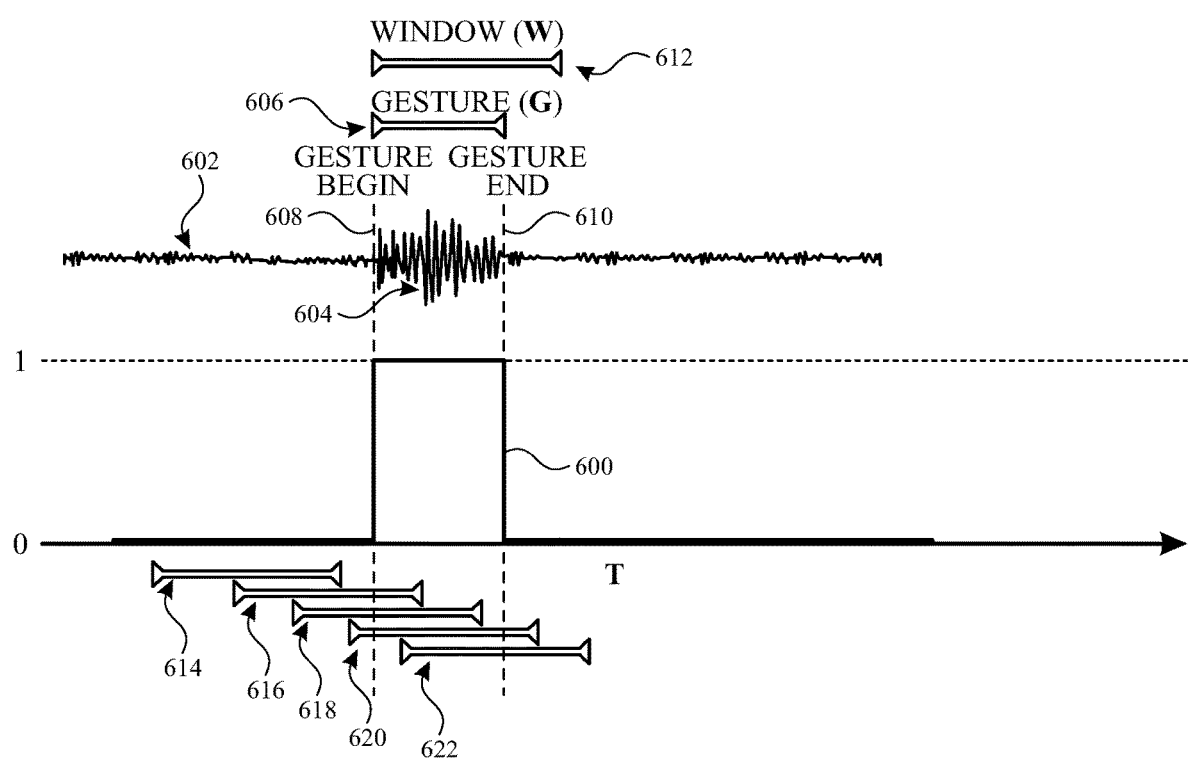
FIG. 6 illustrates an example diagram of a binary label for sensor data that may indicate a gesture in accordance with one or more implementations.

In one or more implementations, a machine learning model (e.g., machine learning model 304) may generate, for the data in a data buffer (e.g., a data buffer storing sensor data from a particular window of time), a confidence output (see, e.g., confidence output 416) or a confidence value (see, e.g., confidence value 420) that indicates whether the data in the data buffer indicates a particular gesture being performed by a user. In one or more implementations, the machine learning model may also be arranged and trained to generate labels for whether a gesture is occurring (e.g., a binary gesture/no-gesture label, a start label and an end label, and/or a smoothly continuous gesture label and/or no-gesture label). FIG. 6 illustrates an example in which the machine learning model generates a binary gesture/no-gesture label 600.

As shown in FIG. 6, for sensor data 602 that includes a portion 604 corresponding to a gesture performed by a user, a gesture/no-gesture label 600 can have a value of, e.g., one when a gesture is being performed and a value of, e.g., zero, when no gesture is being performed. In one or more implementations, the times at which the gesture/no-gesture label 600 transitions from low to high and from high to low can indicate a start time 608 and an end time 610 of a gesture (G) having a gesture duration 606.

As indicated in FIG. 6, a machine learning model such as machine learning model 304 can be run on sensor data collected within a window (W) having a window duration 612. For example, sensor data 602 from a sliding window (W) having a window duration 612, can be loaded into a buffer that is accessible by the machine learning model at each of several times, to provide the sensor data from that window as input to the machine learning model. In the example of FIG. 6, the model may be executed for a window 614 that is entirely before the gesture, windows 616 and 618 that are partially overlapping with the gesture including the beginning of the gesture, a window 620 that includes the entire gesture, and one or more windows such as window 622 that is partially overlapping with the gesture including the end of the gesture. For each of windows 614, 616, 618 620, 622, etc., the model may generate and/or output a binary gesture/no-gesture label 600 indicating whether a gesture is occurring within the window, and a prediction of which gesture is occurring within the window. In one or more implementations, the labels and/or predictions corresponding to multiple windows can be combined to determine a final start time 608, a final end time 610, and/or a final predicted gesture that occurred between the final start time and the final end time.

For example, a machine learning model such as machine learning model 304 may be provided that includes a multi-tasking network head (e.g., at the end of model) to predict the start and end time of the gesture based on the data in the data buffer (e.g., even for windows such as windows 616, 618, or 622 of FIG. 6 in which the start time 608 and/or end time 610 of the gesture may not necessarily be inside the data buffer). For example, the model may be arranged and trained to predict when the gesture actually started and when the gesture is going to end based on the partial information from the gesture that is present in the data buffer at any given time. For example, the machine learning model may include parallel gesture-classification and region-of-interest (ROI) regression heads at the end of the model, the outputs of which can be concatenated for output from the model. The gesture-classification head may generate, for example, a prediction of which gesture is being performed. The ROI regression head may generate, for example, the gesture and/or no-gesture labels for determining the start time and the end time of the gesture being classified, and/or generate the predicted start time and/or predicted end time based on the generated labels.

Multiple gesture start and end timestamps from the rolling prediction windows can be combined to predict the final start and end times for the predicted gesture. For example, aggregated predicted start and end indices corresponding to outputs based on multiple data buffers outputs can be used to identify the start and end indices of a complete gesture, since the multiple data buffers together include the data from the whole gesture duration 606 of the gesture.

In one or more implementations, combining predicted start times and end times for multiple sampling windows can include, for each sampling window, determining a region of interest within that window, converting the region of interest into indices of interest (IOIs) in buffer coordinates, translating the IOIs in buffer coordinates to IOIs respective to a common gating period, aggregating the translated IOIs into an aggregated IOI, and translating the aggregated IOI into index coordinates with an origin at a time equal to zero.

In one or more implementations, a machine learning model that performs multistep prediction during the gesture in this way (e.g., instead of assigning a single prediction to a data buffer), can provide predictions of multiple labels for different parts of the buffer. In this way, the machine learning model can transform a sequence of data in the data buffer into a sequence of labels corresponding to different parts of the buffer.

Although multistep gesture prediction can be performed using a binary gesture/no-gesture label 600 as in the example of FIG. 6, the binary gesture/no-gesture labeling of FIG. 6 may not account for noise in the training data (e.g., due to noisy training labels for the start and end times for a training gesture) and/or noise in the sensor data (e.g., due to user variations in how a gesture is performed). In order to provide a more robust and accurate model, a machine learning model such as machine learning model 304 may be arranged and trained to generate smoothed labels for identifying the start and/or end of a gesture.

Figure 7:
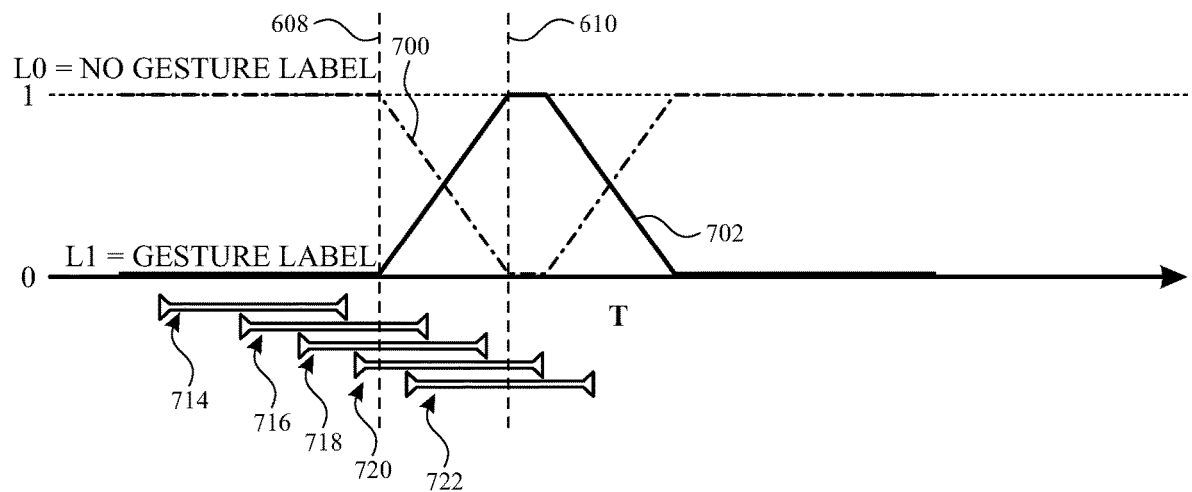
FIG. 7 illustrates an example of smooth labels for a gesture that may be indicated by sensor data in accordance with one or more implementations.

FIG. 7 illustrates an example of smoothed labels for gesture prediction that can be generated using a machine learning model such as machine learning model 304, in one or more implementations. In the example of FIG. 7, the start time 608 and end time 610 of a gesture can be determined using a gesture label 700 and a no-gesture label 702 that can each have multiple values (e.g., discrete or continuous values) between a minimum value (e.g., zero) and a maximum value (e.g., one). As shown, for each of windows 714, 716, 718, 720, 722, etc., the model may generate and/or output both a gesture label 700 (e.g., indicating a probability that a gesture is occurring in that window) and a no-gesture label 702 (e.g., indicating a probability that no gesture is occurring in that window), and a prediction (e.g., classification) of which gesture is occurring within the window.

As indicated in FIG. 7, for a window 714 that does not include any sensor data associated with a gesture, a gesture label 700 may have a minimum value such as a value of zero, and a no-gesture label 702 may have a maximum value such as a value of one. As the rolling or moving window begins to include the gesture, the gesture label 700 begins to (e.g., smoothly) rise and the no-gesture label 702 begins to (e.g., smoothly) decrease until, in window 720 which entirely overlaps the gesture, the gesture label 700 reaches a maximum value (e.g., one) and the no-gesture label 702 reaches a minimum value (e.g., zero). As the rolling or moving window begins to include sensor data obtained after the gesture is complete, the gesture label 700 begins to (e.g., smoothly) decrease and the no-gesture label 702 begins to (e.g., smoothly) rise until, when the window no longer overlaps any portion of the gesture, the gesture label 700 reaches minimum value (e.g., zero) and the no-gesture label 702 reaches a maximum value (e.g., one).

A machine learning model such as machine learning model 304 that predicts the smooth labels of FIG. 7 (e.g., instead of binary label of FIG. 6) can indicate how much of a gesture has been seen by the model, and which gesture has been seen. The model output of a machine learning model that predicts the smooth labels of FIG. 7 can output not only a probability score, but also a prediction (e.g., for each window) of how far the current data in the data buffer extends into the gesture being performed. For example, the values of smooth labels such as the gesture label 700 and the no-gesture label 702 can be generated based on a gesture interval and depending on the size of data buffer in the model, to allow the labels to reflect how much of the gesture overlapped with the data buffer. A thresholding strategy can be applied on top of the smooth predicted labels to determine when the data buffer is mostly or completely inside a gesture being performed (e.g., when the gesture label 700 is above a threshold such as 0.9 and/or when the no-gesture label 702 is below a threshold such as 0.1).

As in the case of binary gesture/no-gesture label 600, in one or more implementations, the model outputs corresponding to the multiple windows 714, 716, 718, 720, 722, etc., can be combined to determine a final start time 608, a final end time 610, and a final predicted gesture that occurred between the final start time and the final end time. In various implementations, the predicted gesture that was previously generated with the highest gesture label 700 and/or the lowest no-gesture label 702 can be used as the final predicted gesture, or the final gesture prediction can be generated after the final start time and final end time have been determined (e.g., by re-running the gesture prediction with the data between the final start time and final end time and thus including the entire gesture).

In one or more implementations, the buffer size for the input data to the machine learning model can be adjusted for the final gesture prediction, based on the final start time 608 and the final end time 610. For example, for a gesture having a gesture duration of 100 milliseconds (ms), a buffer size may be reduced from 1 second to 200 ms for the final gesture prediction (e.g., to avoid including unnecessary and potential confusing data in the buffer). In another example, for a gesture having a gesture duration of 1.3 seconds, a default 1 second buffer size can be increased (e.g., to ensure the sensor data for the entire gesture is included in the buffer) for the final gesture prediction. In one or more implementations, when smooth labels such as the gesture label 700 and the no-gesture label 702 of FIG. 7 are used, instead of cross entropy and softmax functions at the output layer of the machine learning model, binary cross entropy and sigmoid functions can be applied.

Predicting the start and end times of the gesture can be helpful for providing a machine learning model that can detect multi-movement gestures. For example, in order to provide a machine learning model that can predict and/or detect both a single pinch and a double pinch, or both a single clinch and a double clinch, the predicted start and end times can help avoid excluding data corresponding to the second pinch or the second clinch in a double gesture.

Figure 8:
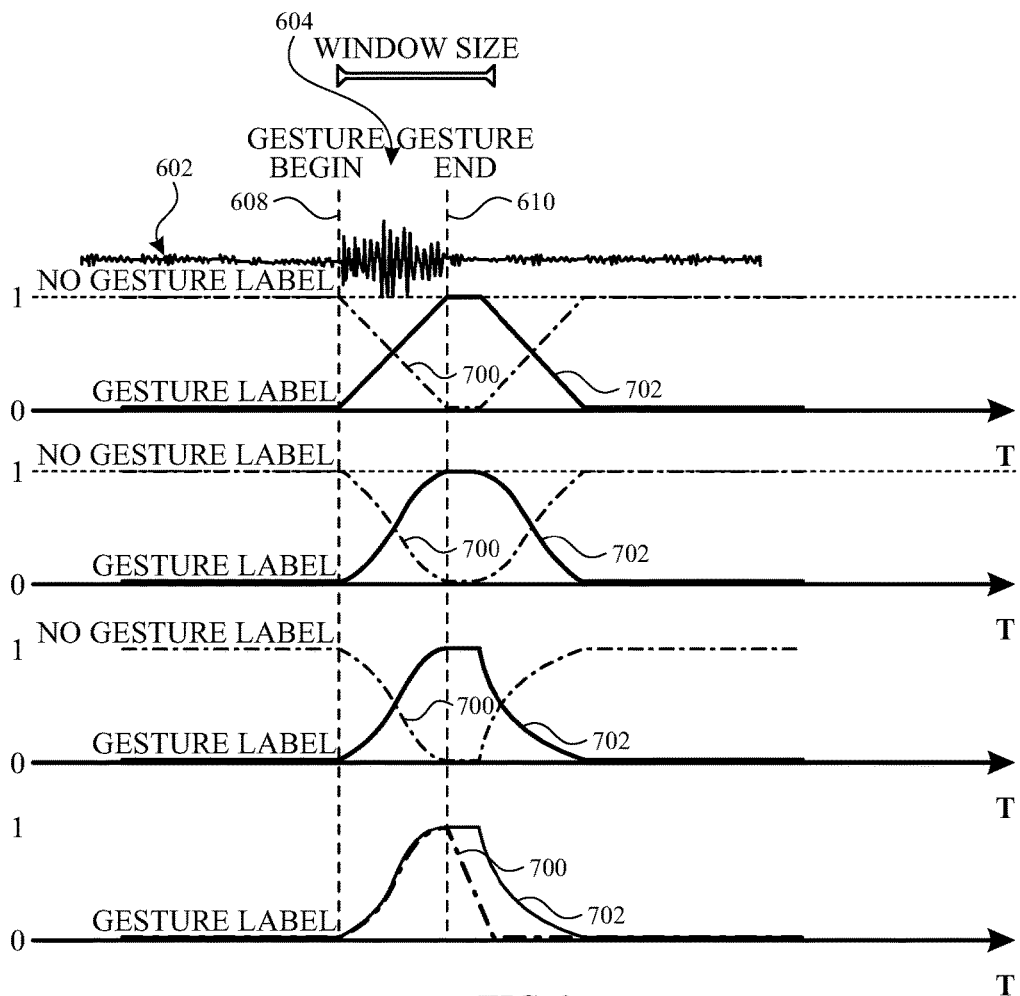
FIG. 8 illustrates additional examples of smooth labels for a gesture that may be indicated by sensor data in accordance with one or more implementations.

It should be appreciated that the gesture label 700 and the no-gesture label 702 shown in FIG. 7, which are linearly increasing or decreasing between minimum and maximum values, are merely illustrative. FIG. 8 illustrates other smooth gesture labels 700 and no-gesture labels 702 that can be used. For example, FIG. 8 illustrates sigmoid and exponential gesture labels 700 and no-gesture labels 702. Providing smooth gesture labels can also include providing an additional score indicating a goodness of a particular window (e.g., a window proposal score), and/or using multi-task learning (e.g., using an additional regressor to indicate which part of a gesture is within a particular prediction window). Although the smooth labeling of FIGS. 7 and 8 are described in the context of gesture detection and/or gesture prediction, it should be appreciated that such smooth labeling of start times and end times in sensor data can be applied to incorporate statistical uncertainty into the labels for other data for detecting occurrences that are limited in time (e.g., for any sensor data for which boundary detection in time-series data is desired so that action can be taken based on the sensor data within or near the boundary or boundaries).

In the examples of FIGS. 6 and 7, the windows 614-622 and 714-722 are used to sample the data uniformly in overlapping sliding windows of time. It should also be appreciated that, in one or more implementations, sampling of data during training of the machine learning model and/or during client use of the machine learning model may be performed pseudo-randomly (e.g., using windows of a common width that are centered at pseudo-random times around the gesture, rather than centered at uniformly progressing times before, during, and after the gesture). Evaluation of the model can be performed using sampling with uniformly progressing windows in one or more implementations.

In one or more implementations, the gesture prediction operations disclosed herein (e.g., using machine learning model 304) can be personalized, or tuned for a specific user. This personalized gesture prediction can be helpful, for example, to provide prediction and/or detection of a gesture performed by a user who typically performs the gesture quickly (e.g., over a first period of time) and also for users who typically perform the gesture slowly (e.g., over a second period of time that is longer than the first period of time). This personalized gesture prediction can also be helpful for prediction and/or detection of a gesture as performed by different users with different physical abilities, for prediction and/or detection of a gesture as indicated by data generated with other static and/or dynamic user variability, for prediction and/or detection of a gesture that varies with movement variability between users, and/or for prediction and/or detection of a gesture generated by users with variations in device-wearing preferences (e.g., variations in band tightness for a smartwatch).

In one example of an implementation including personalized gesture recognition, a device of a user can (e.g., during a gesture registration process for the user and the device, and/or over time during use of the device by the user) build a library of known gestures for that user. Once a library of known gestures is available, the machine learning model may be modified and/or changed from a gesture prediction/recognition model to a gesture matching model, in which new input sensor data is matched to corresponding signal data for one of the gestures in the gesture library, to identify the gesture being performed.

For example, a registration process may be performed for a user for the first time a user is interacting with a machine learning model for gesture prediction and/or recognition. For example, in one or more implementations, a device such as electronic device 102 may provide a request to the user to perform one or more gestures of interest, and register the performed gestures as their way of performing the gesture. A machine learning model such as machine learning model 304 may then use these registered user-specific gestures as training data for better identifying specific types of gestures for that specific user. In this way, the user can customize the gestures according to the way (e.g., the speed or any physical abilities or preferences) the user is comfortable performing the gestures, and the gesture prediction/recognition model can adapt to the user's behavior.

In another example of personalized gesture recognition, personalized federated learning operations can be performed to train and/or to tune or personalize a machine learning model to identify or predict gestures performed by a particular user.

For example, in one or more implementations, a machine learning model such as machine learning model 304 may utilize the federated learning technique to train and/or refine the model across multiple decentralized devices holding local samples, without exchanging samples or aggregating multiple model updates from decentralized mobile devices. In this way, multiple users can contribute to training a common model, while preserving the privacy of the users by avoiding sharing user information between users.

In one or more implementations, a machine learning model can be trained using a federated learning technique to obtain a common initial model trained in the manner described above, and can then be further trained locally at the user's device to be customized to a specific user (e.g., using a gesture registration process or sample data from the specific user and device for model personalization).

Figure 9:
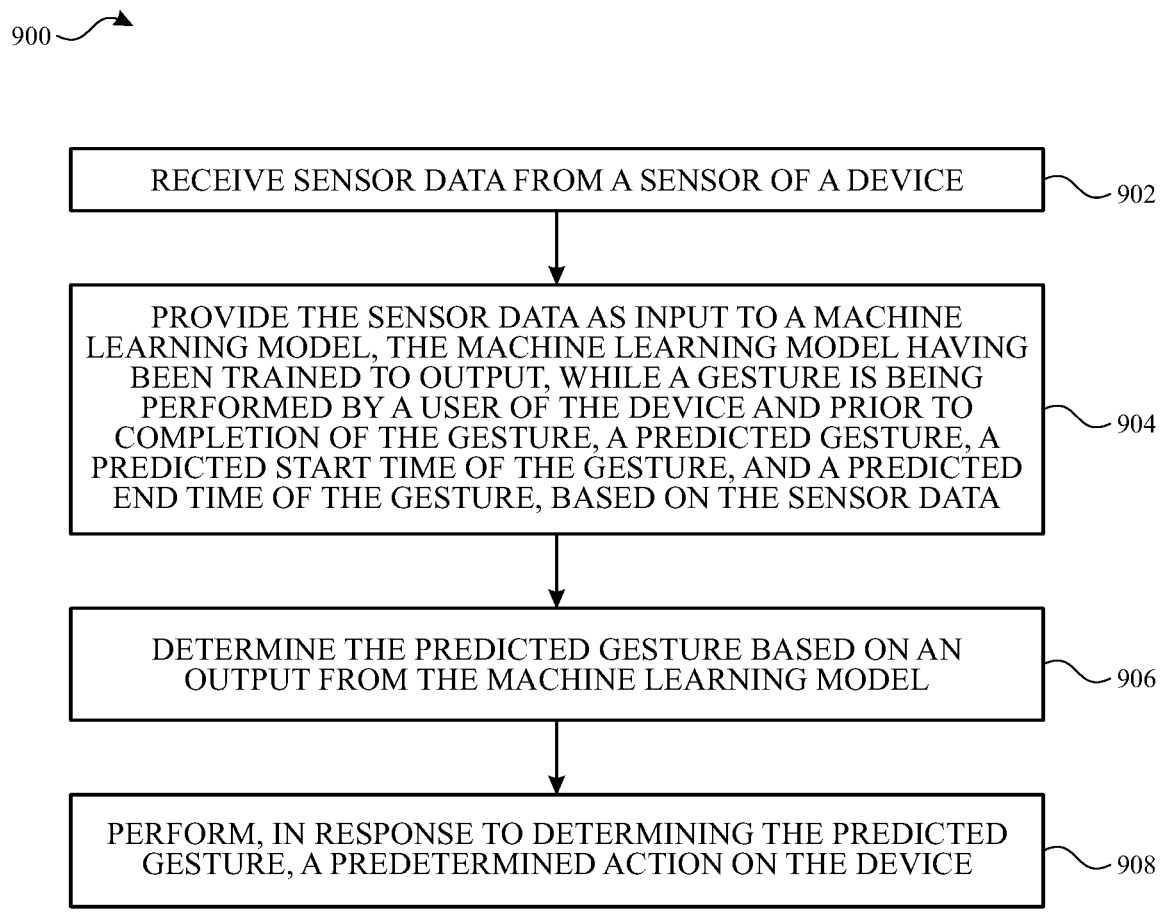
FIG. 9 illustrates a flow diagram of another example process for machine-learning based gesture recognition in accordance with one or more implementations.

FIG. 9 illustrates a flow diagram of example process for machine-learning based gesture recognition in accordance with one or more implementations. For explanatory purposes, the process 900 is primarily described herein with reference to the electronic device 102 of FIG. 1. However, the process 900 is not limited to the electronic device 102 of FIG. 1, and one or more blocks (or operations) of the process 900 may be performed by one or more other components and other suitable devices (e.g., any of the electronic devices 102-104). Further for explanatory purposes, the blocks of the process 900 are described herein as occurring in serial, or linearly. However, multiple blocks of the process 900 may occur in parallel. In addition, the blocks of the process 900 need not be performed in the order shown and/or one or more blocks of the process 900 need not be performed and/or can be replaced by other operations.

At block 902, sensor data may be received from a sensor of a device such as electronic device 102. The sensor data may include biosignal sensor(s) 206 such as from a photoplethysmography (PPG) sensor. The PPG sensor may include at least one of an infrared light source or a color light source. In one or more implementations, the first sensor output may indicate a change in blood flow. The sensor data may include sensor data from one or more of the non-biosignal sensor(s) 208. The non-biosignal sensor(s) 208 may be an accelerometer and/or a microphone, for example. Receiving the sensor data may be based on a determination (e.g., by a mode detection head of the machine learning model) that the device is in a gesture detection mode. Receiving the sensor data may include receiving the sensor data during a first window of time that at least partially overlaps a gesture time (e.g., gesture duration 606) of the gesture. Additional sensor data from the sensor of the device may also be received during one or more additional windows of time such as a second window of time that at least partially overlaps the gesture time of the gesture.

At block 904, the sensor data may be provided as input to a machine learning model (e.g., machine learning model 304), the machine learning model having been trained to output, while a gesture is being performed by a user of the device and prior to completion of the gesture, a predicted gesture, a predicted start time (e.g., start time 608) of the gesture, and a predicted end time (e.g., end time 610) of the gesture, based on the sensor data. In one or more implementations, additional sensor data (e.g., from the second window of time and/or one or more additional windows of time) may also be provided as input to the machine learning model. In one or more implementations, the machine learning model may have been trained to output the predicted start time of the gesture and the predicted end time of the gesture at least in part by generating a gesture label such as gesture label 700 and a no-gesture label such as no-gesture label 702 for each of multiple windows of time (e.g., as described above in connection with FIGS. 7 and 8). For example, the gesture label and the no-gesture label may each have a value that is smoothly continuous (e.g., linearly continuous, exponentially continuous, sigmoid continuous, or otherwise continuous) between a maximum value and a minimum value.

At block 906, the predicted gesture may be determined based on an output from the machine learning model. In one or more implementations, determining the predicted gesture based on the output from the machine learning model may include determining the predicted gesture based on the output from the model that is based on the sensor data from the first window of time and based on an additional output of the machine learning model that is based on the additional sensor data from the second window of time. Determining the predicted gesture based on the output from the machine learning model that is based on the sensor data from the first window of time and the additional output of the machine learning model that is based on the additional sensor data from the second window of time may include aggregating a first predicted start time from the machine learning model that is based on the sensor data from the first window of time and a second predicted start time from the machine learning model that is based on the additional sensor data from the second window of time to determine a final predicted start time for the gesture. Determining the predicted gesture based on the output from the machine learning model that is based on the sensor data from the first window of time and the additional output of the machine learning model that is based on the additional sensor data from the second window of time may include aggregating a first predicted end time from the machine learning model that is based on the sensor data from the first window of time and a second predicted end time from the machine learning model that is based on the additional sensor data from the second window of time to determine a final predicted end time for the gesture. In one or more implementations, a size of an input buffer for the machine learning model may be adjusted (e.g., increased or decreased) based on the final predicted start time and the final predicted end time (e.g., to include all of the sensor data between the final predicted start time and the final predicted end time corresponding to the data for the entire gesture).

Determining the predicted gesture may include determining the predicted gesture at a time after the final predicted end time using sensor data in the input buffer having the adjusted size.

At block 908, in response to determining the predicted gesture, a predetermined action may be performed on the device.

As described above, one aspect of the present technology is the gathering and use of data available from specific and legitimate sources for gesture recognition. The present disclosure contemplates that in some instances, this gathered data may include personal information data that uniquely identifies or can be used to identify a specific person. Such personal information data can include demographic data, location-based data, online identifiers, telephone numbers, email addresses, home addresses, data or records relating to a user's health or level of fitness (e.g., vital signs measurements, medication information, exercise information), date of birth, or any other personal information.

The present disclosure recognizes that the use of such personal information data, in the present technology, can be used to the benefit of users. For example, the personal information data can be used for gesture recognition. Accordingly, use of such personal information data may facilitate transactions (e.g., on-line transactions). Further, other uses for personal information data that benefit the user are also contemplated by the present disclosure. For instance, health and fitness data may be used, in accordance with the user's preferences to provide insights into their general wellness, or may be used as positive feedback to individuals using technology to pursue wellness goals.

The present disclosure contemplates that those entities responsible for the collection, analysis, disclosure, transfer, storage, or other use of such personal information data will comply with well-established privacy policies and/or privacy practices. In particular, such entities would be expected to implement and consistently apply privacy practices that are generally recognized as meeting or exceeding industry or governmental requirements for maintaining the privacy of users. Such information regarding the use of personal data should be prominently and easily accessible by users, and should be updated as the collection and/or use of data changes. Personal information from users should be collected for legitimate uses only. Further, such collection/sharing should occur only after receiving the consent of the users or other legitimate basis specified in applicable law. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations which may serve to impose a higher standard. For instance, in the US, collection of or access to certain health data may be governed by federal and/or state laws, such as the Health Insurance Portability and Accountability Act (HIPAA); whereas health data in other countries may be subject to other regulations and policies and should be handled accordingly.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of gesture recognition, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing identifiers, controlling the amount or specificity of data stored (e.g., collecting location data at city level rather than at an address level), controlling how data is stored (e.g., aggregating data across users), and/or other methods such as differential privacy.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data.

Figure 10:
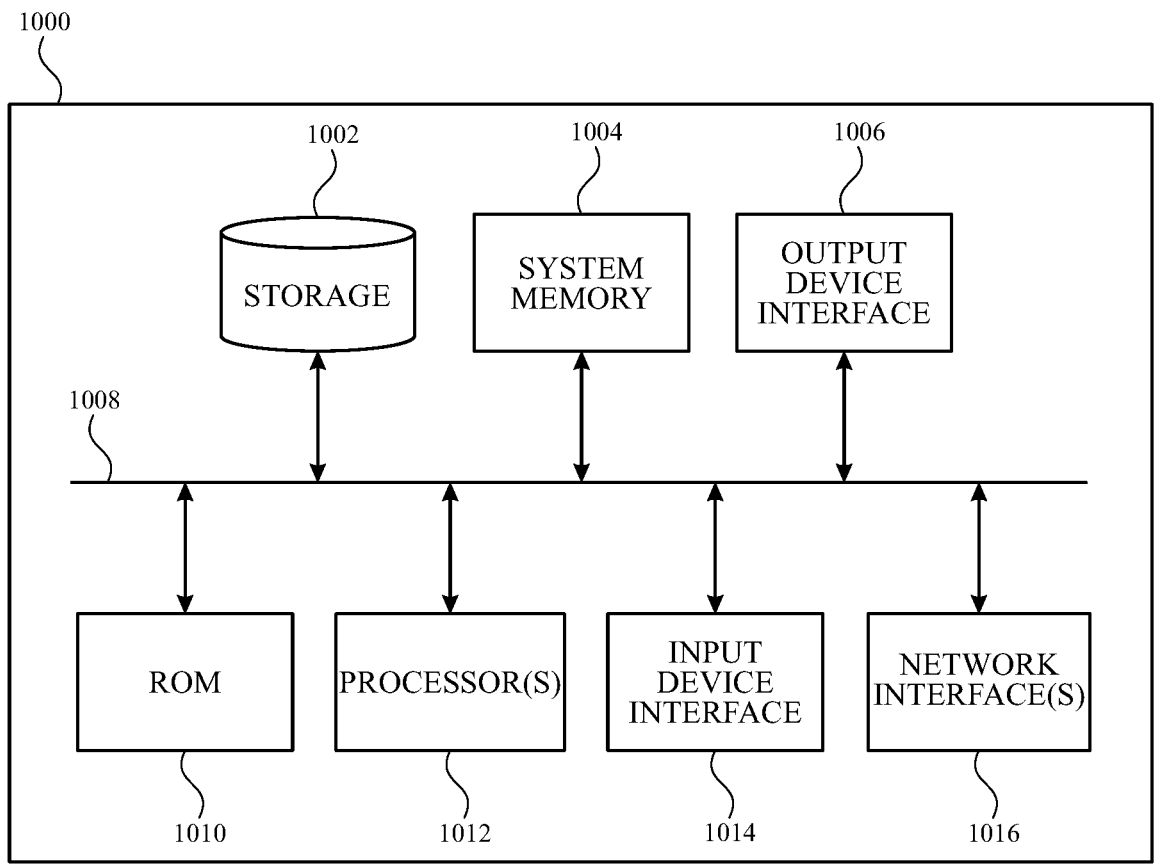
FIG. 10 illustrates an example electronic system with which aspects of the subject technology may be implemented in accordance with one or more implementations.

FIG. 10 illustrates an electronic system 1000 with which one or more implementations of the subject technology may be implemented. The electronic system 1000 can be, and/or can be a part of, one or more of the electronic devices 102-104, and/or one or the server 108 shown in FIG. 1. The electronic system 1000 may include various types of computer readable media and interfaces for various other types of computer readable media. The electronic system 1000 includes a bus 1008, one or more processing unit(s) 1012, a system memory 1004 (and/or buffer), a ROM 1010, a permanent storage device 1002, an input device interface 1014, an output device interface 1006, and one or more network interfaces 1016, or subsets and variations thereof.

The bus 1008 collectively represents all system, peripheral, and chipset buses that communicatively connect the numerous internal devices of the electronic system 1000. In one or more implementations, the bus 1008 communicatively connects the one or more processing unit(s) 1012 with the ROM 1010, the system memory 1004, and the permanent storage device 1002. From these various memory units, the one or more processing unit(s) 1012 retrieves instructions to execute and data to process in order to execute the processes of the subject disclosure. The one or more processing unit(s) 1012 can be a single processor or a multi-core processor in different implementations.

The ROM 1010 stores static data and instructions that are needed by the one or more processing unit(s) 1012 and other modules of the electronic system 1000. The permanent storage device 1002, on the other hand, may be a read-and-write memory device. The permanent storage device 1002 may be a non-volatile memory unit that stores instructions and data even when the electronic system 1000 is off. In one or more implementations, a mass-storage device (such as a magnetic or optical disk and its corresponding disk drive) may be used as the permanent storage device 1002.

In one or more implementations, a removable storage device (such as a floppy disk, flash drive, and its corresponding disk drive) may be used as the permanent storage device 1002. Like the permanent storage device 1002, the system memory 1004 may be a read-and-write memory device. However, unlike the permanent storage device 1002, the system memory 1004 may be a volatile read-and-write memory, such as random access memory. The system memory 1004 may store any of the instructions and data that one or more processing unit(s) 1012 may need at runtime. In one or more implementations, the processes of the subject disclosure are stored in the system memory 1004, the permanent storage device 1002, and/or the ROM 1010. From these various memory units, the one or more processing unit(s) 1012 retrieves instructions to execute and data to process in order to execute the processes of one or more implementations.

The bus 1008 also connects to the input and output device interfaces 1014 and 1006. The input device interface 1014 enables a user to communicate information and select commands to the electronic system 1000. Input devices that may be used with the input device interface 1014 may include, for example, alphanumeric keyboards and pointing devices (also called "cursor control devices"). The output device interface 1006 may enable, for example, the display of images generated by electronic system 1000. Output devices that may be used with the output device interface 1006 may include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more implementations may include devices that function as both input and output devices, such as a touchscreen. In these implementations, feedback provided to the user can be any form of sensory feedback, such as visual feedback, auditory feedback, or tactile feedback; and input from the user can be received in any form, including acoustic, speech, or tactile input.

Finally, as shown in FIG. 10, the bus 1008 also couples the electronic system 1000 to one or more networks and/or to one or more network nodes, such as the server 108 shown in FIG. 1, through the one or more network interface(s) 1016. In this manner, the electronic system 1000 can be a part of a network of computers (such as a LAN, a wide area network ("WAN"), or an Intranet, or a network of networks, such as the Internet. Any or all components of the electronic system 1000 can be used in conjunction with the subject disclosure.

Implementations within the scope of the present disclosure can be partially or entirely realized using a tangible computer-readable storage medium (or multiple tangible computer-readable storage media of one or more types) encoding one or more instructions. The tangible computer-readable storage medium also can be non-transitory in nature.

The computer-readable storage medium can be any storage medium that can be read, written, or otherwise accessed by a general purpose or special purpose computing device, including any processing electronics and/or processing circuitry capable of executing instructions. For example, without limitation, the computer-readable medium can include any volatile semiconductor memory, such as RAM, DRAM, SRAM, T-RAM, Z-RAM, and TTRAM. The computer-readable medium also can include any non-volatile semiconductor memory, such as ROM, PROM, EPROM, EEPROM, NVRAM, flash, nvSRAM, FeRAM, FeTRAM, MRAM, PRAM, CBRAM, SONOS, RRAM, NRAM, racetrack memory, FJG, and Millipede memory.

Further, the computer-readable storage medium can include any non-semiconductor memory, such as optical disk storage, magnetic disk storage, magnetic tape, other magnetic storage devices, or any other medium capable of storing one or more instructions. In one or more implementations, the tangible computer-readable storage medium can be directly coupled to a computing device, while in other implementations, the tangible computer-readable storage medium can be indirectly coupled to a computing device, e.g., via one or more wired connections, one or more wireless connections, or any combination thereof.

Instructions can be directly executable or can be used to develop executable instructions. For example, instructions can be realized as executable or non-executable machine code or as instructions in a high-level language that can be compiled to produce executable or non-executable machine code. Further, instructions also can be realized as or can include data. Computer-executable instructions also can be organized in any format, including routines, subroutines, programs, data structures, objects, modules, applications, applets, functions, etc. As recognized by those of skill in the art, details including, but not limited to, the number, structure, sequence, and organization of instructions can vary significantly without varying the underlying logic, function, processing, and output.

While the above discussion primarily refers to microprocessor or multi-core processors that execute software, one or more implementations are performed by one or more integrated circuits, such as ASICs or FPGAs. In one or more implementations, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

As used in this specification and any claims of this application, the terms "base station", "receiver", "computer", "server", "processor", and "memory" all refer to electronic or other technological devices. These terms exclude people or groups of people. For the purposes of the specification, the terms "display" or "displaying" means displaying on an electronic device.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to", "operable to", and "programmed to" do not imply any particular tangible or intangible modification of a subject, but, rather, are intended to be used interchangeably. In one or more implementations, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

Phrases such as an aspect, the aspect, another aspect, some aspects, one or more aspects, an implementation, the implementation, another implementation, some implementations, one or more implementations, an embodiment, the embodiment, another embodiment, some implementations, one or more implementations, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

The word "exemplary" is used herein to mean "serving as an example, instance, or illustration". Any embodiment described herein as "exemplary" or as an "example" is not necessarily to be construed as preferred or advantageous over other implementations. Furthermore, to the extent that the term "include", "have", or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for".

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more". Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

What is claimed is:

1. A method, comprising:
   receiving sensor data from a sensor of a device;
   providing the sensor data as input to a machine learning model, the machine learning model having been trained to output, while a gesture is being performed by a user of the device and prior to completion of the gesture, a predicted gesture, a predicted start time of the gesture, and a predicted end time of the gesture, based on the sensor data;
   determining the predicted gesture based on an output from the machine learning model; and
   performing, in response to determining the predicted gesture, a predetermined action on the device.

2. The method of claim 1, wherein receiving the sensor data comprises receiving the sensor data during a first window of time that at least partially overlaps a gesture time of the gesture, the method further comprising:
   receiving additional sensor data from the sensor of the device during a second window of time that at least partially overlaps the gesture time of the gesture;
   providing the additional sensor data as input to the machine learning model; and
   determining the predicted gesture based on the output from the machine learning model that is based on the sensor data from the first window of time and based on an additional output of the machine learning model that is based on the additional sensor data from the second window of time.

3. The method of claim 2, wherein determining the predicted gesture based on the output from the machine learning model that is based on the sensor data from the first window of time and based on the additional output of the machine learning model that is based on the additional sensor data from the second window of time comprises:
   aggregating a first predicted start time from the machine learning model that is based on the sensor data from the first window of time and a second predicted start time from the machine learning model that is based on the additional sensor data from the second window of time to determine a final predicted start time for the gesture; and
   aggregating a first predicted end time from the machine learning model that is based on the sensor data from the first window of time and a second predicted end time from the machine learning model that is based on the additional sensor data from the second window of time to determine a final predicted end time for the gesture.

4. The method of claim 3, further comprising adjusting a size of an input buffer for the machine learning model based on the final predicted start time and the final predicted end time.

5. The method of claim 4, wherein determining the predicted gesture comprises determining the predicted gesture at a time after the final predicted end time using sensor data in the input buffer having the adjusted size.

6. The method of claim 1, the machine learning model having been trained to output the predicted start time of the gesture and the predicted end time of the gesture at least in part by generating a gesture label and a no-gesture label for each of multiple windows of time.

7. The method of claim 6, wherein the gesture label and the no-gesture label each have a value that is smoothly continuous between a maximum value and a minimum value.

8. The method of claim 1, wherein the predetermined action corresponds to changing a user interface on the device.

9. The method of claim 1, wherein the predetermined action comprises sending gesture information or an instruction from the device to a companion device.

10. A device, comprising:
    at least one processor; and
    a memory including instructions that, when executed by the at least one processor, cause the at least one processor to:
       receive sensor data from a sensor of the device;
       provide the sensor data as input to a machine learning model, the machine learning model having been trained to output, while a gesture is being performed by a user of the device and prior to completion of the gesture, a predicted gesture, a predicted start time of the gesture, and a predicted end time of the gesture, based on the sensor data;
       determine the predicted gesture based on an output from the machine learning model; and
       perform, in response to determining the predicted gesture, a predetermined action on the device.

11. The device of claim 10, wherein the one or more processors are configured to receive the sensor data during a first window of time that at least partially overlaps a gesture time of the gesture, and are further configured to:
    receive additional sensor data from the sensor of the device during a second window of time that at least partially overlaps the gesture time of the gesture;
    provide the additional sensor data as input to the machine learning model; and
    determine the predicted gesture based on the output from the machine learning model that is based on the sensor data from the first window of time and based on an additional output of the machine learning model that is based on the additional sensor data from the second window of time.

12. The device of claim 11, wherein the one or more processors are configured to determine the predicted gesture based on the output from the machine learning model that is based on the sensor data from the first window of time and based on the additional output of the machine learning model that is based on the additional sensor data from the second window of time by:
    aggregating a first predicted start time from the machine learning model that is based on the sensor data from the first window of time and a second predicted start time from the machine learning model that is based on the additional sensor data from the second window of time to determine a final predicted start time for the gesture; and aggregating a first predicted end time from the machine learning model that is based on the sensor data from the first window of time and a second predicted end time from the machine learning model that is based on the additional sensor data from the second window of time to determine a final predicted end time for the gesture.

13. The device of claim 12, wherein the one or more processors are further configured to adjust a size of an input buffer for the machine learning model based on the final predicted start time and the final predicted end time.

14. The device of claim 13, wherein the one or more processors are configured to determine the predicted gesture at a time after the final predicted end time, using sensor data in the input buffer having the adjusted size.

15. The device of claim 10, the machine learning model having been trained to output the predicted start time of the gesture and the predicted end time of the gesture at least in part by generating a gesture label and a no-gesture label for each of multiple windows of time.

16. The device of claim 15, wherein the gesture label and the no-gesture label each have a value that is smoothly continuous between a maximum value and a minimum value.

17. The device of claim 10, further comprising the sensor.

18. The device of claim 17, wherein the device comprises a smartwatch.

19. The device of claim 18, wherein the at least one processor is configured to receive the sensor data from the sensor of the device while the smartwatch is worn on a wrist of the user, and wherein the gesture corresponds to a single-handed gesture performed by a hand that is coupled to the wrist on which the smartwatch is worn.

20. A non-transitory computer-readable medium storing instructions which, when executed by one or more processors, cause the one or more processors to perform operations comprising:

receiving sensor data from a sensor of a device;
providing the sensor data as input to a machine learning model, the machine learning model having been trained to output, while a gesture is being performed by a user of the device and prior to completion of the gesture, a predicted gesture, a predicted start time of the gesture, and a predicted end time of the gesture, based on the sensor data;
determining the predicted gesture based on an output from the machine learning model; and
performing, in response to determining the predicted gesture, a predetermined action on the device.

21. The non-transitory computer-readable medium of claim 20, wherein receiving the sensor data comprises receiving the sensor data during a first window of time that at least partially overlaps a gesture time of the gesture, the operations further comprising:

receiving additional sensor data from the sensor of the device during a second window of time that at least partially overlaps the gesture time of the gesture;
providing the additional sensor data as input to the machine learning model; and
determining the predicted gesture based on the output from the machine learning model that is based on the sensor data from the first window of time and based on an additional output of the machine learning model that is based on the additional sensor data from the second window of time.

22. The non-transitory computer-readable medium of claim 21, wherein determining the predicted gesture based on the output from the machine learning model that is based on the sensor data from the first window of time and based on the additional output of the machine learning model that is based on the additional sensor data from the second window of time comprises:

aggregating a first predicted start time from the machine learning model that is based on the sensor data from the first window of time and a second predicted start time from the machine learning model that is based on the additional sensor data from the second window of time to determine a final predicted start time for the gesture; and aggregating a first predicted end time from the machine learning model that is based on the sensor data from the first window of time and a second predicted end time from the machine learning model that is based on the additional sensor data from the second window of time to determine a final predicted end time for the gesture.

23. The non-transitory computer-readable medium of claim 22, the operations further comprising adjusting a size of an input buffer for the machine learning model based on the final predicted start time and the final predicted end time.

24. The non-transitory computer-readable medium of claim 23, wherein determining the predicted gesture comprises determining the predicted gesture at a time after the final predicted end time, using sensor data in the input buffer having the adjusted size.

25. The non-transitory computer-readable medium of claim 20, the machine learning model having been trained to output the predicted start time of the gesture and the predicted end time of the gesture at least in part by generating a gesture label and a no-gesture label for each of multiple windows of time.

26. The non-transitory computer-readable medium of claim 25, wherein the gesture label and the no-gesture label each have a value that is smoothly continuous between a maximum value and a minimum value.

27. The non-transitory computer-readable medium of claim 20, wherein the predetermined action corresponds to changing a user interface on the device.

28. The non-transitory computer-readable medium of claim 20, wherein the predetermined action comprises sending gesture information or an instruction from the device to a companion device.

* * * * *